United States Patent
Dihora (10) Patent No.: US 12,302,933 B2
(45) Date of Patent: May 20, 2025

(54) FLAVOR DELIVERY SYSTEM

(71) Applicant: TRUCAPSOL LLC, Bethlehem, PA (US)

(72) Inventor: Jiten Dihora, Center Valley, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 0 days.

(21) Appl. No.: 17/848,345

(22) Filed: Jun. 23, 2022

(65) Prior Publication Data
US 2022/0408771 A1    Dec. 29, 2022

Related U.S. Application Data

(60) Provisional application No. 63/215,169, filed on Jun. 25, 2021.

(51) Int. Cl.
| | | |
|---|---|---|
| A23L 27/10 | (2016.01) | |
| A23J 3/22 | (2006.01) | |
| A23P 30/20 | (2016.01) | |
| A61K 8/92 | (2006.01) | |
| A61Q 11/00 | (2006.01) | |

(52) U.S. Cl.
CPC .............. *A23L 27/10* (2016.08); *A23J 3/227* (2013.01); *A23P 30/20* (2016.08); *A61K 8/922* (2013.01); *A61Q 11/00* (2013.01); *A23V 2002/00* (2013.01)

(58) Field of Classification Search
CPC .......... A23L 27/10; A23L 27/70; A23J 3/227; A23P 30/20; A61K 8/922; A61K 2800/56; A61K 8/97; A61Q 11/00; A23V 2002/00; A23V 2000/00
USPC ........................................................ 426/634
See application file for complete search history.

(56) References Cited

U.S. PATENT DOCUMENTS

| | | | |
|---|---|---|---|
| 2,573,900 A * | 11/1951 | Freeman ................ | C11B 7/0066 552/545 |
| 3,345,358 A | 10/1967 | Inklaar | |
| 3,819,838 A | 6/1974 | Smith et al. | |
| 3,870,542 A | 3/1975 | Ida et al. | |
| 3,943,949 A * | 3/1976 | Ashton ................ | A61C 15/041 132/321 |
| 4,076,774 A | 2/1978 | Short | |
| 4,626,471 A | 12/1986 | Chao | |
| 4,752,485 A * | 6/1988 | Sharma ................ | A61K 9/1617 426/5 |
| 4,818,539 A * | 4/1989 | Shaw .................... | A61K 9/5047 426/74 |
| 5,015,527 A | 5/1991 | Chao | |
| 5,126,151 A * | 6/1992 | Bodor ...................... | A23G 4/20 426/453 |
| 5,227,446 A | 7/1993 | Denzinger et al. | |
| 5,431,930 A * | 7/1995 | Patel ...................... | A23G 4/066 426/3 |
| 5,550,189 A | 8/1996 | Qin et al. | |
| 5,574,179 A | 11/1996 | Wahl et al. | |
| 5,601,760 A | 2/1997 | Rosenberg | |
| 5,837,747 A | 11/1998 | Soon-Shiong et al. | |
| 6,248,909 B1 | 6/2001 | Akimoto et al. | |
| 6,465,016 B2 | 10/2002 | Parikh et al. | |
| 6,572,919 B2 | 6/2003 | Westland et al. | |
| 6,596,073 B1 | 7/2003 | Nyssen et al. | |
| 6,855,335 B2 | 2/2005 | Seok et al. | |
| 7,431,986 B2 | 10/2008 | Van Lengerich et al. | |
| 8,900,495 B2 | 12/2014 | Pacorel et al. | |
| 8,993,041 B2 | 3/2015 | To et al. | |
| 9,205,395 B2 | 12/2015 | Yan | |
| 9,332,774 B2 | 5/2016 | Nakhasi et al. | |
| 9,416,050 B2 | 8/2016 | Seidl et al. | |
| 9,427,719 B2 | 8/2016 | Viaud-Massuard et al. | |
| 9,714,397 B2 | 7/2017 | Feng et al. | |
| 9,937,477 B2 | 4/2018 | Zhang et al. | |
| 9,944,886 B2 | 4/2018 | Hitchcock et al. | |
| 9,993,401 B2 | 6/2018 | Barnett et al. | |
| 10,188,593 B2 | 1/2019 | Dihora et al. | |
| 11,179,302 B2 | 11/2021 | Dardelle | |
| 11,344,502 B1 | 5/2022 | Dihora et al. | |
| 11,465,117 B2 | 10/2022 | Bachawala et al. | |
| 11,484,857 B2 | 11/2022 | Bachawala et al. | |
| 11,542,392 B1 | 1/2023 | Multari | |
| 11,547,978 B2 | 1/2023 | Bachawala et al. | |
| 11,571,674 B1 | 2/2023 | Dihora et al. | |

(Continued)

FOREIGN PATENT DOCUMENTS

| | | |
|---|---|---|
| CA | 1049335 A | 2/1979 |
| CN | 114539887 A | 5/2022 |

(Continued)

OTHER PUBLICATIONS

NPL Diglyceride (Retrieved on Jan. 28, 2025). (Year: 2025).*
NPL Glyceride (Retrieved on Jan. 28, 2025). (Year: 2025).*
U.S. Appl. No. 16/287,509, filed Feb. 27, 2019.
U.S. Appl. No. 16/682,862, filed Nov. 13, 2019.
U.S. Appl. No. 16/830,152, filed Mar. 25, 2020.
U.S. Appl. No. 16/853,003, filed Apr. 20, 2020.
U.S. Appl. No. 17/517,816, filed Nov. 3, 2021.
U.S. Appl. No. 16/776,828, filed Jan. 30, 2020.
U.S. Appl. No. 16/776,965, filed Jan. 30, 2020.
U.S. Appl. No. 16/777,048, filed Jan. 30, 2020.
U.S. Appl. No. 17/724,141, filed Apr. 19, 2022.
U.S. Appl. No. 17/724,166, filed Apr. 19, 2022.

(Continued)

*Primary Examiner* — Erik Kashnikow
*Assistant Examiner* — Bhaskar Mukhopadhyay
(74) *Attorney, Agent, or Firm* — Caesar Rivise, PC (57) ABSTRACT

Disclosed are controlled release particles including: (a) a flavor oil; (b) a plant derived fat; (c) a plant derived wax; (d) a plant derived surfactant; and (e) optionally an anti-oxidant. The particles are particularly useful as a flavor delivery system of a personal care product, an oral care product, a powdered food product, a fluid food product, a powdered nutritional supplement, a fluid nutritional supplement, a bakery dough, a dairy product, a savory food product, a noodle bowl and a non-animal based meat analogue.

14 Claims, 2 Drawing Sheets

(56) References Cited

U.S. PATENT DOCUMENTS

| | | |
|---|---|---|
| 2002/0169233 A1 | 11/2002 | Schwantes |
| 2004/0017017 A1 | 1/2004 | Van Lengerich et al. |
| 2004/0033264 A1 | 2/2004 | Sawhney |
| 2005/0272628 A1 | 12/2005 | Meli et al. |
| 2005/0276831 A1 | 12/2005 | Dihora et al. |
| 2007/0122455 A1* | 5/2007 | Myers ............... A61K 9/006 424/439 |
| 2008/0085297 A1 | 4/2008 | Dave et al. |
| 2008/0103265 A1 | 5/2008 | Schocker et al. |
| 2008/0167188 A1 | 7/2008 | Fischer et al. |
| 2009/0209661 A1 | 8/2009 | Somerville Roberts et al. |
| 2010/0011610 A1 | 1/2010 | Bittorf et al. |
| 2010/0028451 A1 | 2/2010 | Kaplan et al. |
| 2011/0052680 A1 | 3/2011 | Hendrickson et al. |
| 2011/0268778 A1 | 11/2011 | Dihora et al. |
| 2011/0268802 A1 | 11/2011 | Dihora et al. |
| 2012/0128752 A1 | 5/2012 | Loo et al. |
| 2013/0004617 A1 | 1/2013 | Zhang et al. |
| 2013/0022654 A1 | 1/2013 | Deshmukh et al. |
| 2013/0084379 A1 | 4/2013 | Gregson et al. |
| 2013/0239429 A1 | 9/2013 | Vella et al. |
| 2014/0199244 A1 | 7/2014 | Rijcken et al. |
| 2014/0335032 A1 | 11/2014 | Panandiker et al. |
| 2015/0252312 A1 | 9/2015 | De Villeneuve et al. |
| 2016/0038428 A1 | 2/2016 | Harel et al. |
| 2016/0128944 A1 | 5/2016 | Chawrai et al. |
| 2016/0158121 A1 | 6/2016 | Lei et al. |
| 2016/0166480 A1 | 6/2016 | Lei et al. |
| 2016/0206561 A1 | 7/2016 | Kohane et al. |
| 2016/0228338 A9 | 8/2016 | Dihora et al. |
| 2017/0165627 A1 | 6/2017 | Duan et al. |
| 2018/0015009 A1 | 1/2018 | Soubiran et al. |
| 2018/0042825 A1 | 2/2018 | Lei et al. |
| 2019/0275490 A1 | 9/2019 | Bachawala |
| 2021/0045409 A1 | 2/2021 | Witteveen et al. |
| 2022/0133603 A1 | 5/2022 | Bachawala et al. |
| 2023/0060181 A1 | 3/2023 | Dihora et al. |

FOREIGN PATENT DOCUMENTS

| | | | |
|---|---|---|---|
| EP | 0076515 A1 | 4/1983 | |
| EP | 0361677 B2 | 11/1993 | |
| EP | 0815743 A2 | 1/1998 | |
| EP | 1371410 A1 | 12/2003 | |
| EP | 1797946 A2 | 6/2007 | |
| GB | 2363964 A * | 1/2002 | ............... A23G 3/36 |
| JP | H0284147 A * | 3/1990 | |
| RU | 2351364 C2 * | 4/2009 | ........... A23G 3/0017 |
| WO | 9901214 A1 | 1/1999 | |
| WO | 0105926 A1 | 1/2001 | |
| WO | 03013538 A1 | 2/2003 | |
| WO | 2004064971 A2 | 8/2004 | |
| WO | WO 2006024411 A2 | 3/2006 | |
| WO | 2007135583 A2 | 11/2007 | |
| WO | 2008118133 A2 | 10/2008 | |
| WO | WO 2009098226 A1 | 8/2009 | |
| WO | 2011041395 A2 | 4/2011 | |
| WO | 2015091877 A1 | 6/2015 | |
| WO | 2016071151 A1 | 5/2016 | |
| WO | 2017023830 A1 | 2/2017 | |
| WO | WO 2020195132 A1 | 10/2020 | |

OTHER PUBLICATIONS

Jardine. (2022). Amino-functionalized polysaccharide derivatives: Synthesis, properties and application. Current Research in Green and Sustainable Chemistry 5, 100309.

Gasparini et al. (2020). Quantification of residual perfume by Py-GC-MS in fragrance encapsulate polymeric materials intended for biodegradation tests. Molecules, 25, 718.

Larson et al. (2017). Bulky polar additives that greatly reduce the viscosity of concentrated solutions of therapeutic monoclonal antibodies. Journal of Pharmaceutical Sciences, 106, 1211-1217.

Guo et al. (2012). Structure-activity relationship for hydrophobic salts as viscosity-lowering excipients for concentrated solutions of monoclonal antibodies. Pharm Res, 3102-3109.

Kumar et al. (2017). Viscosity-reducing bulky-salt excipients prevent gelation of protein, but not carbohydrate, solutions. Appl Biochem Biotechnol, 1491-1496.

Wang et al. (2021). Hofmeister effect on the viscosity properties of gelatin in dilute solutions. Colloids and Surfaces B: Biointerfaces, 206, 111944.

OECD 301D method (OECD 1992, Test No. 301 Ready Biodegradability, OECD Guidelines for the Testing of Chemicals, Section 3, OECD Publishing, Paris, https://doi.org/10.1787/9789264070349-en.

Thakore et al. (2001). "Studies on biodegradability, morphology and thermo-mechanical properties of LDPE/ modified starch blends." European polymer journal, 37(1), 151-160.

Adhesives Magazine (2016). SARTOMER: Acrylate Oliogmer. Available at: https://www.adhesivesmag.com/articles/94922-sartomer-acrylate-oligomer.

Leung et al. (2017). Enteric coating of micron-size drug particles through a Würster fluid-bed process. Powder Technology, 317, 247-252.

Luo et al. (2014). Zein-based micro-and nano-particles for drug and nutrient delivery: A review. Journal of Applied Polymer Science, 131(16): 40696, 1-12.

Silverajah et al. (2012). Mechanical, thermal and morphological properties of poly (lactic acid)/epoxidized palm olein blend. Molecules, 17(10), 11729-11747.

Tmakova et al. (2015). Plant-derived surfactants as an alternative to synthetic surfactants: surface and antioxidant activities. Chemical Papers, 70(2), 188-196.

Werner et al. (2007). Air-suspension particle coating in the food industry: Part I—State of the art. Powder Technology, 171(1), 25-33.

English language abstract for WO 2009098226 A1 (2009).

English language abstract for WO 2020195132 A1 (2020).

http://polymerdatabase.com/polymer%20physics/sigma.html downloaded on Apr. 29, 2022.

Ko et al., "Characterization of hydrophilic-hydrophobic polymeric surfaces by contact angle measurements", Journal of Colloid and Interface Science, vol. 82(1) (1981).

* cited by examiner

FLAVOR DELIVERY SYSTEM

CROSS-REFERENCE TO RELATED APPLICATIONS

This application claims the benefit of U.S. Provisional Patent App. No. 63/215,169, filed Jun. 25, 2021, the contents of which application are incorporated herein by reference in their entireties for all purposes.

BACKGROUND OF THE INVENTION

Field of Invention

This invention relates to a flavor delivery system, methods for preparing a flavor delivery system, and food products containing the flavor delivery system.

Description of Related Art

A meat analogue is a food product that matches the appearance, flavor, and texture that result from the cooking of certain types of meat, but generally utilizes non-animal derived proteins. These types of products are also referred to as meat analogues, meat alternatives, meat substitutes, mock meat, faux meat, imitation meat, vegetarian mean, or vegan meat. Meat substitutes are desired by persons seeking to reduce or eliminate consumption of certain types of meat and achieve the reduction of fat while maintaining the same perception of fat. Often this perception of fat is delivered by flavor, the rate of absorption of the flavor, the intensity of the flavor, and the quantity of flavor absorbed.

Flavor oils are volatile materials that are prone to oxidative degradation. Loss of flavor molecules during transport in the supply chain and during cooking of food can change the hedonics of the flavor, and significantly reduce the intensity. Flavor oils act to influence perceived intensity in two ways: binding to olfactory receptors and binding to taste receptors. Reducing the volatility of flavor oil is a way to retain flavor molecules and provide a more intense olfactive flavor when the food item is consumed. One aspect of the invention is to provide a composition that reduces the volatility of flavor oil.

The presence of protein generally reduces the impact of flavor. The presence of fat generally increases the perception of flavor. While not being limited to theory, it is postulated that proteins adsorb to taste receptors and surfaces readily because they are amphiphilic in nature (having both negatively charged acid moieties, and positively charged amine moieties). Such absorption can prevent the absorption of flavor by taste receptors because flavors are generally insoluble in proteins and will not diffuse through the absorbed protein to the taste receptors (proteins are highly water soluble, whereas fats are water insoluble). This reduced absorption of flavor by the taste receptors results in a lower perceived intensity of flavor in the mouth. Fats are hydrophobic, water insoluble materials. Absorption of these materials onto taste receptors enables flavors to also be absorbed, because flavors are hydrophobic materials that are generally soluble in fats, allowing for flavor molecules to diffuse into the fat and reach the taste receptors, providing a higher perceived intensity of flavor in the mouth. Thus, it is desired to incorporate flavor in an edible food product such that both fat and flavor could be released at the same time and provide a superior intensity of flavor.

Due to the degradation of flavor oil over time, producers tend to use very large amounts of flavor oil in edible foods to compensate for the degradation and/or loss of flavor oils. The increase in fat (as a vehicle to deliver and stabilize flavor) and flavor content impacts the nutritional value of the product as well as the overall cost of the product.

Examples of flavor delivery systems include solid matrix particles that are formed by dehydration of an oil-in-water emulsion (CA 1049335A), or by gelation utilizing a water-in-oil emulsion (US 20210045409 A1), or by melt processing (US 20130084379 A1). Solid matrix particles are made by a process in which a flavor oil is dispersed into a solution of water-soluble polysaccharide. The dispersion is spray dried by atomizing said dispersion into a stream of hot air to form particles. Solid matrix particles comprising flavor oil encapsulated in a starch matrix require water for flavor release. Such an approach is an efficient manner of delivering flavor if a recipe involves dissolution of the flavor particle. In edible product recipes that do not utilize water, such particles may get caramelized if incorporated into meat substitutes that require cooking at high temperatures, permanently locking in the flavor and/or causing oxidation of the flavor.

US 20210045409 A1 utilizes a blend of fat and flavor that is then gelled with starch or carbohydrate. Such a fat delivery system is made by mixing modified food starch and preservatives in water, then incorporating fat to make an oil-in-water emulsion, then adding gellable polysaccharides and flavor oil, and finally freezing the suspension to yield a solid material. It is not clear how the solid material is transformed into particles. Example 2 of the published application teaches incorporation of flavor in the solid material; however, the composition of flavor in the solid material is only 3.5 wt. %. Hence, US 20210045409 A1 is designed to be a fat delivery system, not a flavor delivery system. The solid material composition requires preservatives due to the presence of starch and water, and preservatives are often not desired in food products, especially organic and vegetarian meat substitutes.

US 20130084379 A1 teaches a delivery system in the form of a solid dispersion that is made by incorporating an active material into a sugar alcohol, heating said mixture to 200° C., then atomizing said heated mixture into a cold liquid oil to collect particles. Such process conditions could be detrimental in the case where the active material is a flavor oil. It is desired to melt process flavor oils at temperature less than the boiling temperature of the flavor oil.

Accordingly, it is desired to provide compositions of flavor delivery systems that utilize low temperature melt processing to yield solid particles comprising fats, waxes, and surfactants such that they are edible, utilize plant-based materials, have a high concentration of flavor oil, do not need preservatives, and can be released during cooking of edible food even in the absence of water. It is further desired to provide flavor delivery systems that remain stable during processing, during incorporation into an edible product formulation, and/or during transport, storage and distribution of the edible product formulation. It is further desired to provide a flavor delivery system that provides matrix ingredients that enhance the absorption of flavor.

All references cited herein are incorporated herein by reference in their entireties. The citation of any reference is not to be construed as an admission that it is prior art with respect to the instant invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

Accordingly, a first aspect of the invention comprises controlled release particle comprising: (a) a flavor oil; (b) a plant derived fat; (c) a plant derived wax; (d) a plant derived surfactant; and (e) optionally an anti-oxidant.

In certain embodiments, the particle comprises 5-35 wt. % of the flavor oil; 40-67 wt. % of the plant derived fat; 18-40 wt. % of the plant derived wax; 0.2-2 wt. % of the plant derived surfactant; and optionally 0-2% of the anti-oxidant.

In certain embodiments, the flavor oil is at least one member selected from the group consisting of plant extracts, fruit extracts, artificial flavors, essential oils, flavor enhancers, and flavors that mimic meat flavors.

In certain embodiments, the plant derived fat is based on at least one member selected from the group consisting of coconut, palm, cocoa, illip, shea, avocado, jojoba, sunflower, almond, rice, tea and vegerite. Preferably, the fat or fat mixture is chosen such that it has a melting point above 40° C., or above 60° C., or above 80° C.

In certain embodiments the plant derived wax is a member selected from the group consisting of floral waxes, hydrogenated oil waxes, candelilla wax, carnauba wax, berry wax, fruit wax, sunflower wax, rice bran wax, fatty alcohols, and mixtures thereof. Preferably, the wax or wax mixture is chosen such that it has a melting point above 40° C., or above 60° C., or above 80° C.

In certain embodiments, the anti-oxidant is at least one member selected from the group consisting of Vitamin A, Vitamin C, Vitamin E, folic acid, Beta-carotene, Coenzyme Q10, alpha-tocopherol and polyphenols.

In certain embodiments the plant derived surfactant is selected from plant extracts, glucosides, lecithins, de-oiled lecithins, and mixtures thereof.

In certain embodiments, the controlled release particles have a diameter from 100 microns to less than 5000 microns.

A second aspect of the invention is a composition comprising a plurality of the controlled release particles of the invention, wherein the composition is a personal care product, an oral care product, a powdered food product, a fluid food product, a powdered nutritional supplement, a fluid nutritional supplement, a bakery dough, a dairy product, a savory food product, a noodle bowl and a non-animal based meat analogue (i.e., meat replica or meat substitute product). Suitable edible meat substitute products may comprise a textured vegetable protein that is combined with the flavor delivery system particles.

In certain embodiments of the second aspect of the invention, the composition has at least two different controlled release technologies, which release different flavor compositions and are selected from the group consisting of neat oils, water-triggered release flavor delivery systems, and heat-triggered release flavor delivery systems.

A third aspect of the invention comprises a method the controlled release particles of the invention. The method comprises: (a) heating the plant derived fat and the plant derived wax above melting temperatures thereof to provide a first mixture; (b) mixing the plant derived surfactant and the flavor oil at room temperature and heating to 50° C. in a sealed container to provide a second mixture; (c) dispersing the second mixture into the first mixture to obtain a homogeneous solution; (d) mechanically manipulating the homogeneous solution to provide droplets or extrudates of a desired shape and a desired size; and (e) cooling the formed droplets or extrudates to ambient temperature.

In certain embodiments, the mechanical manipulation procedure may comprise extrusion, prilling, atomization followed by coating onto an edible food product, pastille making using a cooled drum, 3D printing, sheet forming flowed by cutting, dividing, or grinding into a plurality of desired sized particles. Preferably, the flavor delivery system particle size is 50 micrometers to 5000 micrometers, or 100 micrometers to 500 micrometers, or 150 micrometers to 500 micrometers.

A fourth aspect of the invention comprises a method for preparing a finished product composition comprising a plurality of the controlled release particles of the invention, said method comprising the steps of: (a) mixing the flavor delivery system particles with other components of the finished product to deliver 0.001 to 0.75 grams of flavor per gram of finished product composition; and (b) forming the finished product composition via hand molding, automated molding, baking, freezing, frying, extruding, or mixing/blending.

BRIEF DESCRIPTION OF SEVERAL VIEWS OF THE DRAWINGS

The invention will be described in conjunction with the following drawings, wherein the scale shown in each figure is in centimeters, and.

DETAILED DESCRIPTION OF PREFERRED EMBODIMENTS OF THE INVENTION

Glossary

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Particles

The invention addresses one or more of the prior art deficiencies described above by providing controlled release particles.

The inventors have surprisingly found that flavor can be dispersed in fats and waxes by using edible plant-based surfactants that stabilize the flavor without imparting a bitter taste to the flavor delivery system. The inventors have surprisingly found that high concentrations of flavor can be incorporated into compositions which remain a solid at room temperature. The inventors have devised non-aqueous flavor delivery system composition that do not require preservatives. The inventors have developed compositions that can be processed at temperatures less than 100° C., that can be incorporated into edible compositions without premature release of flavor.

In one embodiment, there is provided a plurality of flavor delivery system controlled release particles, each particle comprising: (a) a flavor oil; and (b) a plant derived fat; and (c) a plant derived wax, and (d) a plant derived surfactant, and (e) optionally an anti-oxidant.

In certain embodiments, the flavor delivery system particles comprise 5-35 wt. % of a flavor oil, 40-67 wt. % of a plant derived fat, 18-40 wt. % of a plant derived wax, 0.2-2 wt. % of a plant derived surfactant, and 0-2% anti-oxidant.

In certain embodiments, the flavor is a single flavor agent or combination of two or more flavor agents. Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Suitable flavorants may also include essential oils such as those obtained from thyme, lemongrass, citrus, anise, clove, aniseed, roses, lavender, citronella, *eucalyptus*, peppermint, camphor, sandalwood, cinnamon leaf and cedar. Essential oils that exhibit antimicrobial properties are also contemplated by this invention. The flavor agent may include beef flavor, pork flavor, veal flavor, chicken flavor, duck flavor, turkey flavor, fish flavor, goose flavor, lamb flavor, seafood flavors, fruity flavors, seasoning flavor, herb flavor, taste enhancers, taste modifiers, taste maskers.

In certain embodiments, the plant derived fat is based on coconut, palm, cocoa, fillip shea, avocado, jojoba, sunflower, almond, rice, tea, vegerite, and mixtures thereof. Preferably, the fat or fat mixture is chosen such that it has a melting point above 40° C., or above 60° C., or above 80° C.

In certain embodiments, the plant derived wax is selected from floral waxes such as ylang yland flower wax, jasmine flower wax, lavender flower wax, rose flower wax, *mimosa* flower wax, and the like; hydrogenated oil waxes such as hydrogenated hemp seed oil, hydrogenated soybean oil, hydrogenated castor oil, hydrogenated olive oil, hydrogenated rapeseed oil, hydrogenated avocado oil, hydrogenated vegetable oil, hydrogenated almond oil, and the like; candelilla wax; carnauba wax; berry wax *Rhus* verniciflua peel cera; *myrica* cerifera fruit wax; sunflower wax; rice bran wax; stearyl alcohol; cetearyl alcohol; cetyl alcohol; and mixtures thereof. Preferable, the wax or wax mixture is chosen such that it has a melting point above 40° C., or above 60° C., or above 80° C.

In certain embodiments, the plant derived surfactant is selected from extracts prepared from Sapindus mukorossi, *Verbascum densiflorum, Equisetum arvense, Betula pendula* and *Bellis perennis* (Tmakova, L. et. al.; "Plant Derived Surfactants as an Alternative to Synthetic Surfactants: Surface and Antioxidant Activities," Chemical Papers—Slovak Academy of Sciences, January 2015); coco glucoside, decyl glucoside, lauryl glucoside, sucrose cocoate, caprylyl/capryl glucoside; phospholipids such as de-oiled lecithins from sunflower oil, canola oil, or soy; and mixtures thereof. Phospholipids are preferably selected from lecithins, preferably fluid, deoiled, or fractionated lecithins. Preferred lecithins have greater than 20% by weight of phosphatidylcholine. The oil soluble emulsifier may be a member selected from the group consisting of nonionic surfactants such as polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, sorbitan esters and monoglycerides.

The anti-oxidant is preferably a member selected from the group consisting of vitamins, phytochemicals, and enzymes. Examples of vitamins having antioxidant properties are Vitamin A, Vitamin C, Vitamin E, folic acid, (Beta-carotene), Coenzyme Q10, alpha-tocopherol. Examples of phytochemicals having antioxidant properties include Carotenoids, flavonoid, allyl sulfides, polyphenols. Examples of enzymes that can be used as antioxidants are Superoxide dismutase, glutathione peroxidase, glutathione reductase, catalase. Water soluble antioxidants include grapeseed extract, ascorbic acid, citric acid, and the like.

The controlled release particles are preferably spherical but non-spherical shapes are also within the scope of the invention. The particles preferably have a diameter from 100-5000 microns, or from 250 microns to less than 2000 microns.

Method of Making the Particles

In certain embodiments, a method for preparing the flavor delivery system controlled release particles of the invention, said method comprising: (a) heating the plant derived fat and plant derived wax above the melting temperature; (b) mixing the plant derived surfactant and flavor oil at room temperature and heating to 50° C. in a sealed container; (c) dispersing the flavor mixture into the melted fat/wax mixture to obtain a homogeneous solution; (d) mechanically manipulating the mixture to achieve droplets or extrudates of various shapes in the size range of 100 microns to 5000 microns; (e) cooling the formed droplets or extrudates to ambient temperature. In certain embodiments, the mechanical manipulation procedure may comprise extrusion, prilling, atomization followed by coating onto an edible food product, pastille making using a cooled drum, 3D printing, sheet forming flowed by cutting, dividing, or grinding into a plurality of desired sized particles.

In certain embodiments, the plant derived fat and plant derived wax are melted separately, then mixed at the higher melting temperature. The ability to form distinct particles is a strong function of the melt viscosity of the material. The plant derived fat generally has low melt viscosity, is malleable, smears easily, and makes it difficult to form particles. The formed particles stick to one another and become one solid mass when stored or transported. The incorporation of plant derived wax into the plant derived fat provides a way to change the melt viscosity such that upon cooling the blend of plant derived fat and plant derived wax to room temperature, the transition in viscosity allows one to process the blend into distinct particles that have a low tendency to aggregate, utilizing extrusion as a particle formation technique. The quantity of plant derived wax necessary for blending into a plant derived fat can be ascertained by experimentation and small scale extrusion.

Flavor oil can be homogeneously blended into a blend of plant derived fat and plant derived wax. However, upon cooling, a very low quantity of flavor oil can be stabilized in the blend. As a result, a pool of flavor oil can be observed dissociated from the blend of plant derived wax and plant derived fat in the solid particles. Addition of an oil soluble surfactant increases the quantity of flavor that can be stabilized in the blend.

Addition of anti-oxidant is necessary if the flavor oil composition contains molecules that are highly sensitive to oxidation.

The mixture of flavor oil, surfactant, plant derived fat, plant derived wax, and anti-oxidant can be formed into particles using a variety of techniques. Preferably, the material is extruded. The material can also be transformed into pastilles using a variety of equipment available in the marketplace. The melted material may also be prilled by atomizing the suspension in a tower having a flow of cold air. Alternatively, the melted material may be atomized onto a fluidized bed of ingredients to which the flavor delivery system will be incorporated. The finished product ingredients serve as template particles onto which the flavor delivery system is coated, yielding flavor delivery system particles. Alternatively, the melted material can be poured onto a nonstick parchment paper to achieve a desired thickness, then cooled in a convection oven, released from the parchment paper, and mechanically manipulated to achieve desired shapes and sizes.

Compositions Containing the Particles

The invention further comprises finished product compositions comprising the flavor delivery system controlled release particles. Such compositions include but are not limited to a personal care product, an oral care product, a powdered food product, a fluid food product, a powdered nutritional supplement, a fluid nutritional supplement, a bakery dough, a dairy product, a savory food product, a noodle bowl or cup, a non-animal based meat analogue (or meat replica or meat substitute product). Suitable edible meat substitute product may comprise a textured vegetable protein that is combined with the flavor delivery system particles.

In certain embodiments, the finished product composition comprises a food product that contains an edible base and a desired amount of flavor delivery system controlled release particles. The food product may be a hybrid food product containing a blend of animal-derived components and non-animal derived components. Preferably, the edible food product comprises a vegetarian or vegan meat analogue product. In some embodiments, the food product is a solid or semi-solid food that comprises an edible plant derived protein base and a plurality of flavor delivery systems dispersed within the edible plant derived protein base. The non-animal derived protein base may comprise, without limitation, algae, beans, broccoli, mycoprotein, nuts, peas, potatoes, oatmeal, seeds, plant leaf proteins, seitain, tempeh, tofu, and mixtures thereof.

In certain embodiments, a method for preparing a finished product composition comprising flavor delivery system controlled release particles comprises the steps of: (a) mixing the flavor delivery system particles with the finished product components to deliver 0.001 to 0.75 grams of flavor per gram of finished product composition; and (b) forming the finished product composition via hand molding, automated molding, baking, freezing, frying, extruding, or mixing/blending.

In certain embodiments, the finished product composition comprises a burger patty. A typical plant based burger patty may be formed by blending together reconstituted textured vegetable protein and flavor delivery system controlled release particles. The textured vegetable protein is typically provided as a dehydrated product and can be reconstituted with water or another suitable cooking broth or consumable liquid. The textured vegetable protein is generally ground to a smaller size prior to blending with the flavor delivery system controlled release particles. The blend is formed into suitable sized burger patties by hand, hand tool, or automated burger patty forming equipment.

In certain embodiments, a bakery dough is provided that comprises a flavor delivery system. Specific examples of bakery doughs include, but are not limited to, muffins, crackers, rolls, biscuits, pie crusts, breads, pizza doughs, bagels, and the like.

In certain embodiments, the flavor delivery system particles are incorporated into dairy products. Exemplary dairy products include, but are not limited to, ice cream, ice cream desserts, frozen yogurt, milk, flavored milk drinks, fermented dairy drinks, soy milk, almond milk, coffee creamers, and other dairy-based desserts.

In certain embodiments, the flavor delivery system particles are incorporated into consumable savory products, including but are not limited to, potato chips, crisps, nuts, tortilla-tostada pretzels, cheese snacks, corn snacks, potato snacks, popcorn, crackers, cracker snacks, breakfast cereals, meats, tomato products, peanut butter products, soups, canned vegetables, pasta sauces, noodle bowls, noodles, and bread substitutes.

In certain embodiments, the flavor delivery system particles are incorporated into personal care products listed on the website available at www.cosmeticsinfo.org/whats-my-products.

In certain embodiments, the flavor delivery system particles are incorporated int oral care and oral hygiene products including, but not limited to, toothpastes, toothgels, tooth powders, tooth whitening products, lozenges, throat drops, and the like.

The invention will be illustrated in more detail with reference to the following Examples, but it should be understood that the instant invention is not deemed to be limited thereto.

EXAMPLES

Example 1: Pastilles

Figure 1:
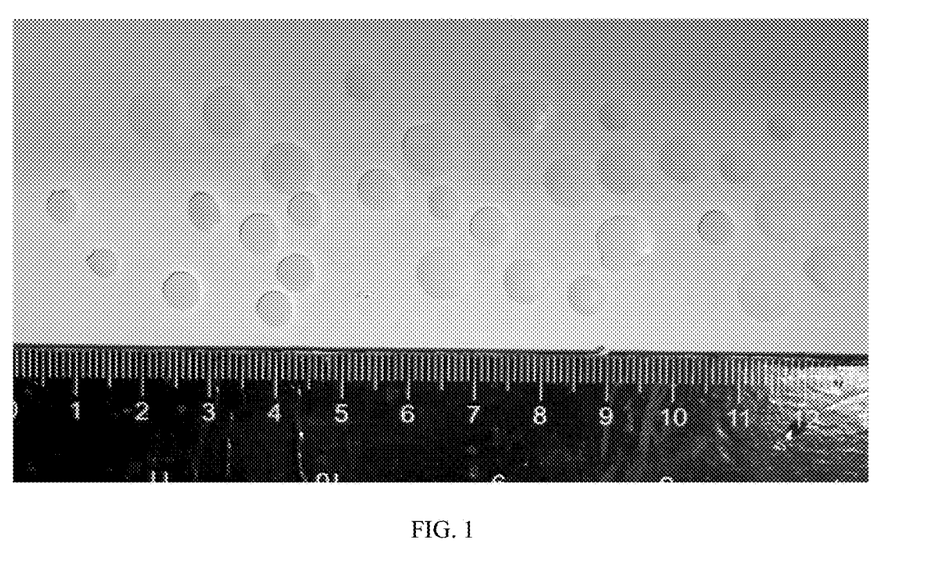
FIG. 1 is a photograph of pastilles of flavor delivery system controlled release particles.

1A: 52.5 grams of palm fat (ADM) is mixed with 21.3 grams of palm wax (Strahl & Pitsch) and heated at 95° C. In a separate container, 1.2 grams of lecithin (Cargill) is mixed with 25 grams of beef flavor (Wild Flavors) and heated to 40° C. Next, the flavor oil blend is added to the palm fat and palm wax blend to create a homogeneous suspension. A syringe is used to develop droplets that fall onto parchment paper. The formed droplets flatten on the parchment paper and when cooled, can be easily removed from the paper using a flat silicone spatula to recover pastilles.

1B. 67.3 grams of palm fat (ADM) is mixed with 27.5 grams of palm wax (Strahl & Pitsch) and heated at 95° C. In a separate container, 0.2 grams of lecithin (Cargill) is mixed with 5 grams of beef flavor (Wild Flavors) and heated to 40° C. Next, the flavor oil blend is added to the palm fat and palm wax blend to create a homogeneous suspension. A syringe is used to develop droplets that fall onto parchment paper. The formed droplets flatten on the parchment paper and when cooled, can be easily removed from the paper using a flat silicone spatula to recover pastilles.

1C. 44.7 grams of palm fat (ADM) is mixed with 18.3 grams of palm wax (Strahl & Pitsch) and heated at 95° C. In a separate container, 2 grams of lecithin (Cargill) is mixed with 35 grams of beef flavor (Wild Flavors) and heated to 40° C. Next, the flavor oil blend is added to the palm fat and palm wax blend to create a homogeneous suspension. A syringe is used to develop droplets that fall onto parchment paper. The formed droplets flatten on the parchment paper and when cooled, can be easily removed from the paper using a flat silicone spatula to recover pastilles.

1D. 40 grams of palm fat (ADM) is mixed with 40 grams of palm wax (Strahl & Pitsch) and heated at 95° C. In a separate container, 0.9 grams of lecithin (Cargill) is mixed with 19.1 grams of beef flavor (Wild Flavors) and heated to 40° C. Next, the flavor oil blend is added to the palm fat and palm wax blend to create a homogeneous suspension. A syringe is used to develop droplets that fall onto parchment paper. The formed droplets flatten on the parchment paper and when cooled, can be easily removed from the paper using a flat silicone spatula to recover pastilles.

Flavor delivery system pastilles are incorporated into a vegetarian burger patty to deliver 0.1 grams of fragrance oil. The patties are cooked. The cooking process melts the flavor delivery system particles, and the beef flavor can be immediately detected. The beef flavor intensity is high upon consuming the burger. A comparative burger patty made with flavor oil only (no flavor delivery system particles) does provide a detectable amount of flavor during cooking, but very little to no flavor (taste or olfactive) during consumption of the burger.

Example 2—Extrudates

Figure 2:
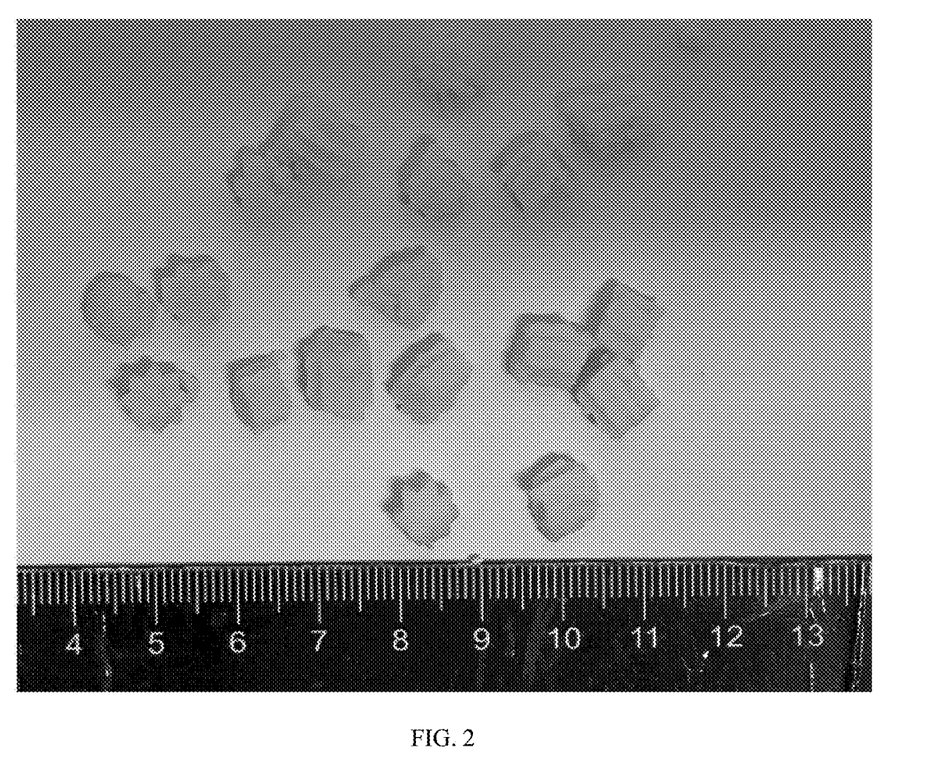
FIG. 2 is a photograph of extrudates of flavor delivery system controlled release particles.

2A: 52.5 grams of palm fat (ADM) is mixed with 21.3 grams of palm wax (Strahl & Pitsch) and heated at 95° C. In a separate container, 1.2 grams of lecithin (Cargill) is mixed with 25 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. The tubular extrudate is allowed to cool to room temperature on parchment paper. The extrudate is sliced into small pieces using a kitchen knife.

2B. 67.3 grams of palm fat (ADM) is mixed with 27.5 grams of palm wax (Strahl & Pitsch) and heated at 95° C. In a separate container, 0.2 grams of lecithin (Cargill) is mixed with 5 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. The tubular extrudate is allowed to cool to room temperature on parchment paper. The extrudate is sliced into small pieces using a kitchen knife.

2C. 44.7 grams of palm fat (ADM) is mixed with 18.3 grams of palm wax (Strahl & Pitsch) and heated at 95° C. In a separate container, 2 grams of lecithin (Cargill) is mixed with 35 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. The tubular extrudate is allowed to cool to room temperature on parchment paper. The extrudate is sliced into small pieces using a kitchen knife.

2D. 40 grams of palm fat (ADM) is mixed with 40 grams of palm wax (Strahl & Pitsch) and heated at 95° C. In a separate container, 0.9 grams of lecithin (Cargill) is mixed with 19.1 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. The tubular extrudate is allowed to cool to room temperature on parchment paper. The extrudate is sliced into small pieces using a kitchen knife.

Such extrudates can be milled to reduce the particle size into the preferred range to assure homogeneity of the flavor delivery system in the finished product formulation, assure an adequate rate of release of the flavor during cooking and chewing.

Flavor delivery system extrudates are incorporated into a vegetarian burger patty to deliver 0.1 grams of fragrance oil. The patties are cooked. The cooking process melts the flavor delivery system particles, and the beef flavor can be immediately detected. The beef flavor intensity is high upon consuming the burger. A comparative burger patty made with flavor oil only (no flavor delivery system particles) does provide a detectable amount of flavor during cooking, but very little to no flavor (taste or olfactive) during consumption of the burger.

Example 3. Beads

Figure 3:
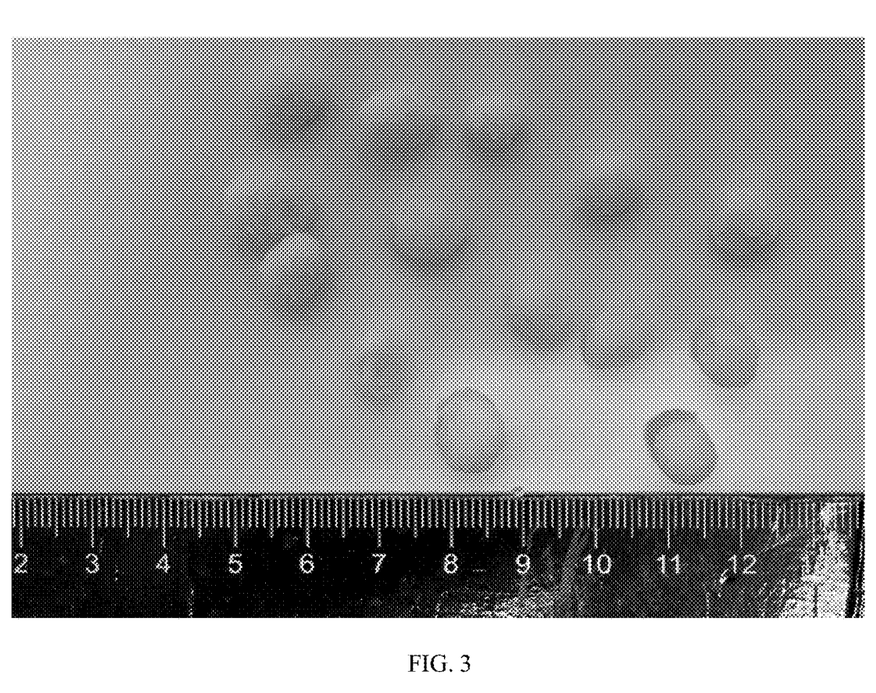
FIG. 3 is a photograph of beads of flavor delivery system controlled release particles.

3A: 52.5 grams of palm fat (ADM) is mixed with 21.3 grams of palm wax (Strahl & Pitsch) and heated at 95° C. In a separate container, 1.2 grams of lecithin (Cargill) is mixed with 25 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. While the tubular extrudate is still warm, small pieces of extrudate are manually rolled into spheres. The spherical beads are then rolled into a fine powder of palm wax in a pan, to achieve a uniform coating, to eliminate agglomeration of the beads.

3B. 67.3 grams of palm fat (ADM) is mixed with 27.5 grams of palm wax (Strahl & Pitsch) and heated at 95° C. In a separate container, 0.2 grams of lecithin (Cargill) is mixed with 5 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. While the tubular extrudate is still warm, small pieces of extrudate are manually rolled into spheres. The spherical beads are then rolled into a fine powder of palm wax in a pan, to achieve a uniform coating, to eliminate agglomeration of the beads.

3C. 44.7 grams of palm fat (ADM) is mixed with 18.3 grams of palm wax (Strahl & Pitsch) and heated at 95° C. In a separate container, 2 grams of lecithin (Cargill) is mixed with 35 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. While the tubular extrudate is still warm, small pieces of extrudate are manually rolled into spheres. The spherical beads are then rolled into a fine powder of palm wax in a pan, to achieve a uniform coating, to eliminate agglomeration of the beads.

3D. 40 grams of palm fat (ADM) is mixed with 40 grams of palm wax (Strahl & Pitsch) and heated at 95° C. In a separate container, 0.9 grams of lecithin (Cargill) is mixed with 19.1 grams of beef flavor (Wild Flavors) and heated to 40° C. Next, the flavor oil blend is added to the palm fat and palm wax blend to create a homogeneous suspension. The mixture is allowed to cool to 40° C., then fed into a hand held extruder/pasta maker containing a single hole at the exit of the extruder. While the tubular extrudate is still warm, small pieces of extrudate are manually rolled into spheres. The spherical beads are then rolled into a fine powder of palm wax in a pan, to achieve a uniform coating, to eliminate agglomeration of the beads.

Flavor delivery system beads are incorporated into a vegetarian burger patty to deliver 0.1 grams of fragrance oil. The patties are cooked. The cooking process melts the flavor delivery system particles including the palm wax powder coating, and the beef flavor can be immediately detected. The beef flavor intensity is high upon consuming the burger. A comparative burger patty made with flavor oil only (no flavor delivery system particles) does provide a detectable amount of flavor during cooking, but very little to no flavor (taste or olfactive) during consumption of the burger.

While the invention has been described in detail and with reference to specific examples thereof, it will be apparent to one skilled in the art that various changes and modifications can be made therein without departing from the spirit and scope thereof.

What is claimed is:

1. A controlled release particle consisting of the following components: (a) a flavor oil; (b) a plant derived fat; (c) a plant derived wax; (d) a plant derived surfactant; and (e) optionally an anti-oxidant, wherein the components are homogeneously distributed throughout the controlled release particle.

2. The controlled release particle of claim 1, consisting of 5-35 wt. % of the flavor oil; 40-67 wt. % of the plant derived fat; 18-40 wt. % of the plant derived wax; 0.2-2 wt. % of the plant derived surfactant; and optionally 0-2% of the anti-oxidant.

3. The controlled release particle of claim 1, wherein the flavor oil is at least one member selected from the group consisting of plant extracts, fruit extracts, artificial flavors, essential oils, flavor enhancers, and flavors that mimic meat flavors.

4. The controlled release particle of claim 1, wherein the plant derived fat is based on at least one member selected from the group consisting of coconut, palm, cocoa, illip, shea, avocado, jojoba, sunflower, almond, rice, tea and vegerite.

5. The controlled release particle of claim 1, wherein the plant derived wax is at least one member selected from the group consisting of floral waxes, hydrogenated oil waxes, candelilla wax, carnauba wax, berry wax, fruit wax, sunflower wax, rice bran wax, and fatty alcohols.

6. The controlled release particle of claim 1, wherein the anti-oxidant is at least one member selected from the group consisting of Vitamin A, Vitamin C, Vitamin E, folic acid, Beta-carotene, Coenzyme Q10, alpha-tocopherol and polyphenols.

7. The controlled release particle of claim 1, wherein the plant derived surfactant is selected from the group consisting of plant extracts, glucosides, lecithins, de-oiled lecithins and mixtures thereof.

8. The controlled release particle of claim 1, which has a diameter from 100 microns to less than 5000 microns.

9. A composition comprising a plurality of the controlled release particle of claim 1, wherein the composition is a personal care product, an oral care product, a powdered food product, a fluid food product, a powdered nutritional supplement, a fluid nutritional supplement, a bakery dough, a dairy product, a savory food product, a noodle bowl or a non-animal based meat analogue.

10. The composition of claim 9, which is configured to release a first flavor composition using a first controlled release technology and to release a second flavor composition different from the first flavor composition using a second controlled release technology different from the first controlled release technology, wherein the first controlled release technology and the second controlled release technology are selected from the group consisting of neat oils, water-triggered release flavor delivery systems, and heat-triggered release flavor delivery systems.

11. A method for preparing the controlled release particle of claim 1, said method comprising:
heating the plant derived fat and the plant derived wax above melting temperatures thereof to provide a first mixture;
mixing the plant derived surfactant and the flavor oil at room temperature and heating to 50° C. in a sealed container to provide a second mixture;
dispersing the second mixture into the first mixture to obtain a homogeneous solution;
mechanically manipulating the homogeneous solution to provide droplets or extrudates of a desired shape and a desired size; and cooling the formed droplets or extrudates to ambient temperature to provide the controlled release particle.

12. The method of claim 11, wherein the mechanical manipulating comprises extrusion, prilling and atomization followed by coating onto an edible food product, pastille making using a cooled drum, 3D printing, sheet forming followed by cutting, dividing, or grinding into a plurality of desired sized particles.

13. A method for preparing a finished product composition comprising a plurality of the controlled release particle of claim 1 as a flavor delivery system, said method comprising the steps of:
  mixing the plurality of the controlled release particle with other components of the finished product composition to deliver 0.001 to 0.75 grams of flavor per gram of the finished product composition; and
  forming the finished product composition via hand molding, automated molding, baking, freezing, frying, extruding, or mixing/blending.

14. The controlled release particle of claim 1, wherein the flavor oil mimics meat flavors and is provided in an amount from 5 to 35 wt. % of the controlled release particle.

\* \* \* \* \*